United States Patent
Nutter et al.

(10) Patent No.: US 6,313,178 B1
(45) Date of Patent: *Nov. 6, 2001

(54) USE OF HEXAHYDROLUPULONES AS ANTIBACTERIAL AND ANTICANCER AGENTS

(75) Inventors: Louise Nutter, Minneapolis, MN (US); Emily O. Ngo, Hamden, CT (US); Gilbert J. Mannering, St. Paul; Thomas Stephan, Minneapolis, both of MN (US)

(73) Assignee: Regents of the University of Minnesota, Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/125,928

(22) Filed: Jul. 28, 1999

Related U.S. Application Data

(63) Continuation of application No. 08/607,473, filed on Feb. 27, 1996.

(51) Int. Cl.⁷ .................................................. A61K 31/12
(52) U.S. Cl. .......................................................... 514/690
(58) Field of Search ............................... 514/689, 690

(56) References Cited

U.S. PATENT DOCUMENTS

| | | | |
|---|---|---|---|
| 4,590,296 | 5/1986 | Cowles et al. | 568/366 |
| 4,918,240 | 4/1990 | Todd, Jr. et al. | 568/366 |
| 5,082,975 | 1/1992 | Todd, Jr. et al. | 568/315 |
| 5,286,506 | 2/1994 | Millis et al. | 426/335 |
| 5,370,863 * | 12/1994 | Barney et al. | 424/49 |
| 5,455,038 | 10/1995 | Barney et al. | 424/405 |
| 5,827,895 * | 10/1998 | Nutter et al. | 514/690 |

OTHER PUBLICATIONS

Carson, J.F., "The Hydrogenatio of Lupulone and Humulone" *Journal of the American Chemical Society,* 73, pp. 1850–1852, (Apr. 1951).

Gomez–Flores, "Enhanced Intramacrophage Aactivity of Resorcinomycin a Against *Mycobacterium avium*–Mycobacterium intracellulare Complex after Liposome Encapsulation", *Antimicrobial Agents & Chemotheraphy,* 40 (11), pp. 2545–2549, (Nov. 1996).

Ji, et al., "How Effective is KRM–1648 in Treatment of Disseminated *Mycobacterium avium* complex Infections in Beige Mice?", *Antimicrobial Agents & Chemotherapy,* 40 (2), pp. 437–442, (Feb. 1996).

Mannering, G.J., et al., "Effects of the Hop Component, Colupulone, on the Induction of Cytochrome P4503A and the Replication of Human Tumour Cells", *Food, Nutrition and Chemical Toxicity,* Chapter 28, Smith–Gordon and Company Limited, London, UK, pp. 311–323, (1993).

Mizobuchi, S., et al., "Antifungal Activities of Hop Bitter Resins and Related Compounds", *Agric. Biol. Chem.,* 49 (2), pp. 399–403, (1985).

Mizobuchi, S., et al., "Antifungal Activities of Hop Bitter Resins and Related Compounds", *Rep. Res. Lab. Kirin Brew. Co.,* No. 28, pp. 39–44, (1985).

Yasukawa, K., et al., "Humulon, a Bitter in the Hop, Inhibits Tumor Promotion by 12–0–Tetradecanoylphorbol–13–Acetate in Two–Stage Carcinogenesis in Mouse Skin", *Oncology,* 52, pp. 156–158, (1995).

* cited by examiner

*Primary Examiner*—Jerome D. Goldberg
(74) *Attorney, Agent, or Firm*—Schwegman, Lundberg, Woessner & Kluth, P.A.

(57) ABSTRACT

The present invention provides pharmaceutical compositions comprising an amount of hydrogenated lupulones or derivatives or analogs thereof, effective to inhibit cancer cell growth, and methods of use thereof.

9 Claims, 1 Drawing Sheet

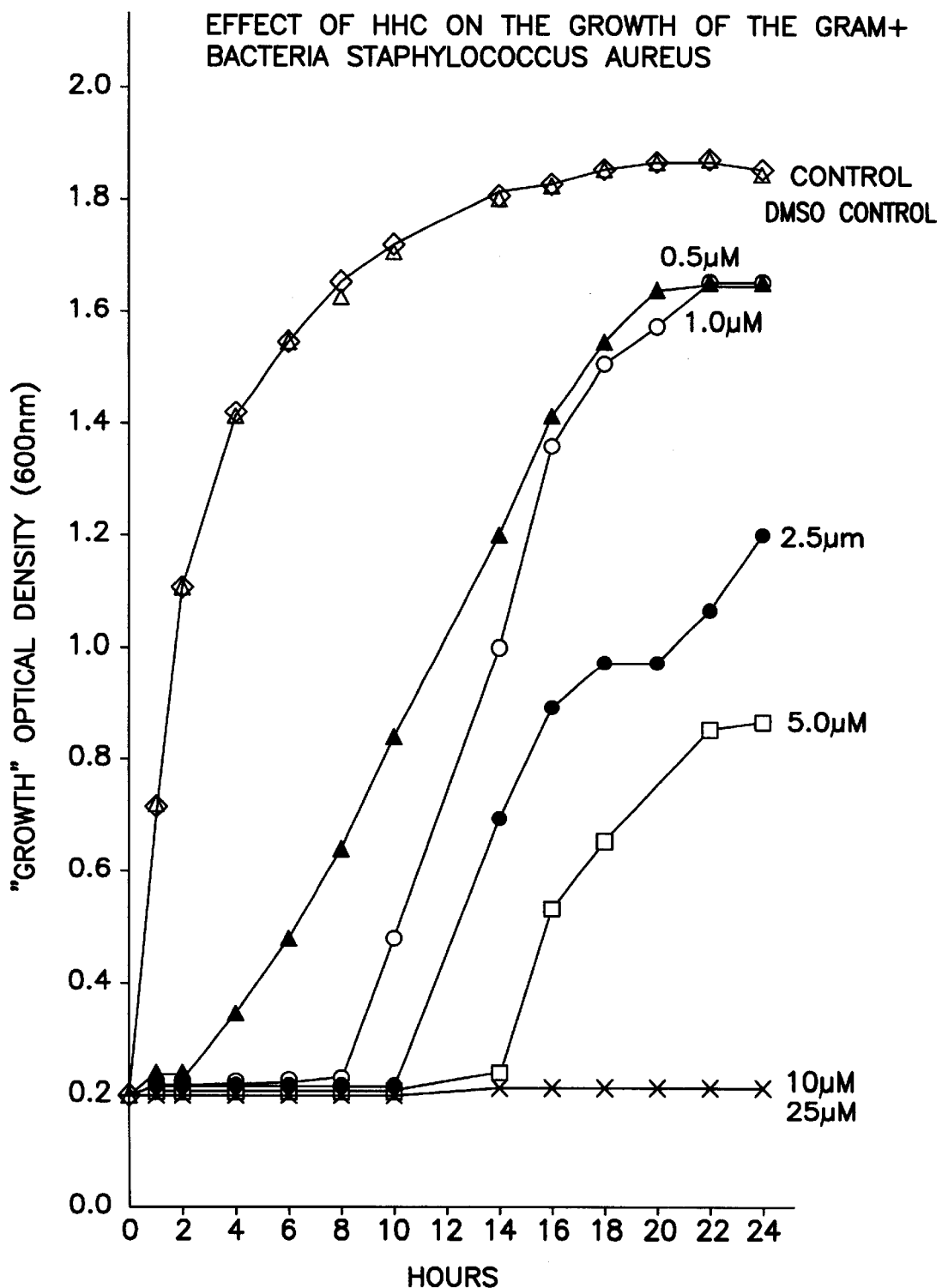

USE OF HEXAHYDROLUPULONES AS ANTIBACTERIAL AND ANTICANCER AGENTS

This application is a 371 of PCT/U.S. Ser. No. 97/03073 filed Sep. 27, 1997 and a continuation of Ser No.08/607,473 filed Feb. 27, 1996.

BACKGROUND OF THE INVENTION

The treatment and/or cure of cancer has been intensely investigated culminating in a wide range of therapies. Cancer has been typically treated with surgery, radiation and chemotherapy, alone or in conjunction with various therapies employing drugs, biologic agents, antibodies, and radioactive immunoconjugates, among others. The common goal of cancer treatment has been, and continues to be, the elimination or amelioration of cancerous tumors and cells with minimal unpleasant or life-threatening side effects, due to toxicity to normal tissues and cells. However, despite efforts, these goals remain largely unmet.

Even where effective non-invasive drug therapies have been developed, patients having solid malignant tumors and hematological malignant disorders often develop multidrug resistance. Current therapies involve the administration of increased dosages of the anticancer drug or drugs to which the cancer cells have become resistant and/or administration of agents designed to reverse drug accumulation defects in drug resistant cells. However, these therapies are limited by risk of toxicity to the patient.

Alpha- and beta-acids, derived from hops, possess the ability to inhibit the growth of microorganisms. Some of these acids have been used as antibiotic and antifungal agents. In addition, alpha acids (also known as humulons) have been shown to inhibit the tumor promoting effect of 12-O-tetradecanoylphorbol-13-acetate in mice (Yasukawa et al., *Oncology* 52:156–158 (1995)). Colupulone has been reported to be active against Hela cells, CEM leukemia cells, and adriamycin- and vinbiastin-resistant CEM cells (Mannering et al., *Food, Nutrition and Chemical Toxicity*, Parke et al., eds, Smith Gordon, G. B. (1993) at ch. 28).

Thus, a need exists for new and effective drug therapies for treating cancer which have minimal side effects and are also effective against multidrug resistant cancer cells.

SUMMARY OF THE INVENTION

The present invention provides a method to inhibit cancer cell growth, and thereby to treat cancer comprising administering to a mammal afflicted with cancer an effective amount of the compound

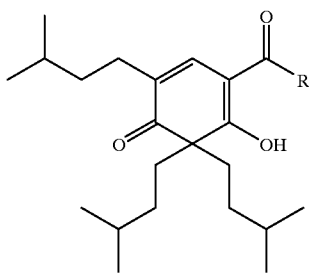

(I)

wherein R is $(C_3-C_8)$alkyl, preferably —CH$_2$CH(CH$_3$)$_2$, —CH(CH$_3$)$_2$, or —CH(CH$_3$)CH$_2$CH$_3$, or a pharmaceutically acceptable salt thereof. In a preferred embodiment of the invention, R is —CH(CH$_3$)$_2$. The present invention further provides a method of inhibiting bacterial cell growth by contacting bacterial cells with an effective amount of a compound of formula (I). The present invention also provides pharmaceutical compositions, such as compositions adapted for topical administration, comprising an effective amount of a compound of formula (I) in combination with a pharmaceutically acceptable carrier. The compounds of the invention are particularly effective against gram positive bacteria, such as mycobacterium strains, including drug-resistant M. tuberculosis strains or Mycobacterial avian complex (MHC). The compounds are also active against S. aureus, including methocillin-resistant S. aureus.

As used herein, the term alkyl encompasses branched and straight-chain alkyl groups, as well as cycloalkyl and (cycloalkyl)alkyl.

BRIEF DESCRIPTION OF THE DRAWINGS

FIG. 1 shows the activity of HHC against *Staphylococcus aureus*.

DETAILED DESCRIPTION OF THE INVENTION

The present invention provides a method of killing cancer cells and/or inhibiting their growth through the use of certain β-acids. In a preferred embodiment, the method utilizes lupulones or analogs thereof. Generally preferred are hydrogenated derivatives of lupulones, e.g., compounds of the formula

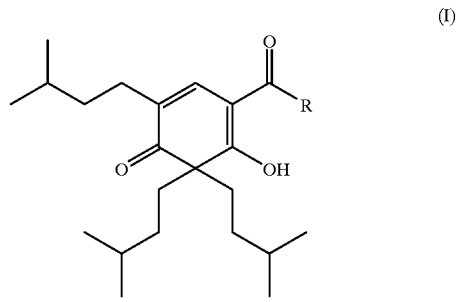

(I)

are used, wherein R is $(C_3-C_8)$alkyl, preferably —CH$_2$CH(CH$_3$)$_2$ (hexahydrolupulone), —CH(CH$_3$)$_2$ (hexahydrocolupulone or "HHC"), or —CH(CH$_3$)CH$_2$CH$_3$ (hexahydroadlupulone), or a pharmaceutically acceptable salt thereof. In a preferred embodiment of the invention, R is —CH(CH$_3$)$_2$. The compounds may also be administered as a mixture comprising one or more compounds of formula (I). The tautomeric forms of the compounds of formula (I) are also within the scope of the present method.

Beta-acids (also known as lupulones), and tetrahydroisohumulone and hexahydrocolupulone in particular, can inhibit the growth of food pathogens, such as Listeria monomcytogenes (U.S. Pat. Nos. 5,286,506; 5,455,038). In addition, hexahydrolupulone inhibits the growth of certain Lactobacilli (U.S. Pat. No. 5,082,975). However, the antineoplastic effects of hydrogenated lupulones have not been previously reported.

These compounds have been found to be highly effective cytostatic and cytotoxic agents which are active against cells of a wide variety of cancers. For example, hexahydrocolupulone has been found to have cytotoxic and/or cytostatic effect against human breast adenocarcinoma cells, human acute lymphoblastic leukemia cells, vinblastin resistant cells, human Burkitt lymphoma cells, human oral epidermoid carcinoma cells, and human cervical epithelioid carcinoma cells.

Hexahydrocolupulone (HHC) has also demonstrated effectiveness against drug resistant human cancer cell lines, for example, vinblastin resistant human acute lymphoblastic leukemia cells. Multidrug resistance against anticancer compounds is one of the most formidable problems in cancer chemotherapy. In addition to their broad spectrum anticancer activity, the compounds of the present invention have potential clinical application due to their high potency, as shown by their relatively low $IC_{50}$ concentrations ($IC_{50}$ represents the concentration of compound required to kill 50% of cancer cells in an in vitro assay). Moreover, as a derivative of a generally-recognized safe hop extract, HHC can be considered negligibly toxic when ingested, an advantage over many existing chemotherapeutic agents.

Hydrogenated lupulones appear to be more active and stable than their non-hydrogenated parent compounds. For example, hexahydrocolupulone is more active than colupulone (see Mannering et al., cited supra) while hexahydrolupulone has been found to be more stable than lupulone (Carson, *J. Amer. Chem. Soc.* 73:1850–1852 (1951)).

According to the invention, cancer cells are inhibited by administration to a mammal afflicted with cancer of an effective amount of the compounds of Formula (I). The "effective amount" will ultimately depend upon whether inhibition of growth or killing of cancer cells is goal of the treatment. However, as described herein, a suitable dose will be in the range of about 0.5 to about 100 mg/kg of body weight per day.

The compositions described herein are believed to be effective in the treatment of solid mammalian tumors or hematologic malignancies, and include those which can develop multidrug resistance. These solid tumors include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. Hematological malignancies include childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

Without being bound by any particular theory regarding mechanism of action, preliminary results using the fluorescent activated cell sorting (FACS) method suggest that HHC has an effect upon the G1-S phase transition of the cell cycle. Other studies suggest that the cytotoxic effect of HHC on cancer cells is not due to major effects upon DNA, RNA or protein synthesis.

In another embodiment of the invention, a compound of formula (I), or a salt or pharmaceutical composition thereof, is used to inhibit bacterial cell growth. In a preferred method, the bacteria is a gram positive bacteria. In a more preferred embodiment, the gram positive bacteria is Staphylococcus aureus. In another preferred embodiment, the bacteria is a mycobacterium. In a more preferred embodiment, the mycobacteria is tuberculosis or mycobacterial avian complex (MHC).

In a further embodiment of the invention, a compound of formula (I), or a salt or a pharmaceutical composition thereof, is useful as a parasiticidal agent, for example as shown in Example VII hereinbelow. The compounds of the invention can be used against the hemoflagellates, such as against leishmania.

Hexahydrolupulones are hydrogenated derivatives of lupulones, a constituent of hops (up to 5–7%). Hexahydrocolupulone can be made via the chemical hydrogenation of colupulone using a number of methods known in the art. For example, hydrogenation can be achieved with platinum (IV) oxide as a catalyst as described by Riedl (Ber. 89:1863 (1956)) or by Carson (*J. Am. Chem. Soc.* 73:1850 (1951)).

In a preferred method, beta-acids are purified as described in U.S. Pat. No. 4,918,240 and hydrogenated as described in U.S. Pat. No. 5,082,975 (both of which are herein incorporated in their entireties). According to a preferred method of purifying beta acids, palladium or platinum catalyst poisons are removed from an aqueous alkaline beta acid solution by agitating the solution at a pH of at least about 10, preferably between about 11 and 12.9, in the presence of polyvalent metals other than palladium and platinum. The insoluble catalyst poison containing materials are then separated.

Preferably, the polyvalent metals used are edible metal ions, preferably magnesium and calcium, and may also be zinc, aluminum or iron. Preferably, the pH is between about 11 and 12.9. Although a solvent is not necessary for removal of the catalyst poisons, water-immiscible food-grade solvents may be used. Examples include hydrocarbons such as hexane, esters, liquid fatty alcohols, and terpenes such as limonen.

In preparation for the ensuing hydrogenation step, the purified beta acids may be recovered from the alkaline aqueous phase by the $CO_2$ method of Cowles (U.S. Pat. No. 4,590,296). Alternatively, the beta-acid solution is mixed with about an equal volume of an organic solvent such as hexane. The beta-acids are extracted into solvent by slow acidification with agitation, using an acid such as phosphoric acid, until a pH of about 9.5–9.8 is reached. Substantially all of the beta acids are removed from the aqueous phase by this procedure. The beta acids may then be recovered from the solvent by partial evaporation and cooling, or by removal of the hexane under vacuum, by procedures known to the art.

Any known method of hydrogenation may be used, although preferably one is used which results in a high purity of beta acids. Preferably, the purified beta-acids are hydrogenated under non-acidic conditions. According to a preferred method, the beta-acids are dissolved in solvent and water. Any non-toxic, non-reactive solvent may be used such as lower alkanols, an organic water miscible or THF. A hydrogenation catalyst such as palladium or platinum is added. The vessel is evacuated, hydrogen gas is introduced, and the vessel is agitated until hydrogen uptake has ceased. The hydrogenated product is filtered to remove the catalyst. A solution of water and a hydrocarbon solvent such as hexane is then added. The mixture is agitated and the hydrogenated beta acid is extracted into the hexane phase. After partial evaporation of the hexane, the mixture is seeded and cooled, allowing the product to crystallize.

To allow conversion to pure hydrogenated beta acids, the minimum pH used is about 3, preferably above 4, with the most preferred range between about 7 to 9. The rate of hydrogenation may be accelerated through the use of additional amounts of catalyst or by raising the temperature.

An aqueous liquid alkaline solution of hydrolupulones may be prepared as described in U.S. Pat. No. 5,082,975. Alternatively, propylene glycol, glycerine, similar stable alcohols and polyols, or mixtures thereof with or without water, may be substituted for the water of the aqueous solution. In addition, the foregoing aqueous solution may be mixed with glycol or glycerine, etc., to form a standardized solution of product, which is readily-dispersible in water, and stable as well.

Pharmaceutically acceptable salts of the biologically active compounds described herein may be used as well in practicing the claimed methods. Pharmaceutically acceptable salts may be formed using organic or inorganic bases, such as NaOH, Na(CO$_3$)$_2$, NaHCO$_3$, KOH, amines and the like.

Although the compounds described herein and/or their its salts may be administered as the pure chemicals, it is preferable to present the active ingredient as a pharmaceutical composition. The invention thus further provides the use of a pharmaceutical composition comprising one or more compounds and/or a pharmaceutically acceptable salt thereof, together with one or more pharmaceutically acceptable carriers therefor and, optionally, other therapeutic and/or prophylactic ingredients. The carrier(s) must be 'acceptable' in the sense of being compatible with the other ingredients of the composition and not deleterious to the recipient thereof.

Pharmaceutical compositions include those suitable for oral or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system. Such methods also include encapsulation of a therapeutically effective amount of the active ingredient in liposomes, by methods known to the art.

Pharmaceutical compositions suitable for oral administration may be presented as discrete unit dosage forms such as hard or soft gelatin capsules, cachets or tablets each containing a predetermined amount of the active ingredient; as a powder, as liposomal preparations, or as granules; as a solution, a suspension or as an emulsion.

Compositions suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; muco-adherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

For topical administration to the epidermis, the active ingredients may be formulated as ointments, creams or lotions, or patches. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis from a suitable reservoir, e.g., as disclosed in U.S. Pat. Nos. 4,140,122; 4,383,529; or 4,051,842.

The active ingredient can be delivered via patches for transdermal administration. Suitable transdermal delivery systems are disclosed, for example, in U.S. Pat. No. 4,788,603, U.S. Pat. No. 4,931,279, U.S. Pat. No. 4,668,506, U.S. Pat. No. 4,713,224 and U.S. Pat. No. 5,560,922. Patches for transdermal delivery can comprise a backing layer and a polymer matrix which has dispersed or dissolved therein an effective amount of the active ingredient, along with one or more skin permeation enhancers. The backing layer can be made of any suitable material which is impermeable to the analogs or derivatives of the invention. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix. The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydro-gel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a penetration agent, such as a fatty alcohol or a glycol such as propylene glycol can be used to increase the permeability of the outermost layer of skin, the stratum corneum, to the therapeutic agent.

The active agent or derivative may also be formulated so as to be suitable for administration by inhalation or insufflation or for nasal, intraocular or other topical (including buccal and sub-lingual) administration. For example, for administration to the upper (nasal) or lower respiratory tract by inhalation, the active agent or derivative is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the active agent may take the form of a dry powder composition, for example, a powder mix of the active agent and a suitable powder base such as lactose or starch. The powder composition may be presented in unit dosage form in, for example, capsules or cartridges or, e.g., gelatin or blister packs from which the powder may be administered with the aid of an inhalator, insufflator or a metered-dose inhaler.

For intra-nasal administration, the active agent may also be administered via nose drops, a liquid spray, such as via a plastic bottle atomizer or metered-dose inhaler. Typical of atomizers are the Mistometer® (Wintrop) and the Medihaler® (Riker).

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The subdose itself may be further divided, e.g., into a number of discrete loosely spaced administrations; such as multiple inhalations from an insufflator or by application of a plurality of drops into the eye.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The following examples are intended to illustrate but not limit the invention.

EXAMPLES

Example I

Cytostatic Activity

HHC was tested for cytostatic activity using the trypan blue exclusion assay. The purpose of the assay is to determine the concentration of HHC at which 50% of cell growth is inhibited (i.e., $ID_{50}$) when cells are continuously exposed to the HHC. Five ml of a mixture of $2 \times 10^5$ cells/ml were placed in T-25 flasks. HHC or control (no HHC or DMSO vehicle) was added. The cells were incubated at 37° C. under 5% $CO_2$ for 24 or 48 hours. Monolayer cells which are attached need to be incubated for a minimum of 14 hours before HHC is added in order to allow the cells to attach. The cells are detached by pancreatinizing (attached cells) and or suspended well (unattached cells). A 100 $\mu$l sample was removed from the cell suspension and placed in a borosilicate glass test tube. One hundred $\mu$l of 0.4% trypan blue solution (trypan blue (Sigma) in phosphate buffered saline) was added to the cell suspension sample and mixed well. The cells were counted using a hemocytometer. $ID_{50}$ was calculated by choosing a drug concentration that was below 50% inhibition as well as a drug concentration that was above 50% inhibition and then interpolating those values to 50% inhibition. The following formula was used:

% inhibition=100-% growth,
where % growth=$[(C_t-C_0)/(C_{ct}-C_0)] \times 100$,
where $C_0$ is the cell count at time "0";
$C_t$ is the cell count of the HHC treated sample at time "t"; and
$C_{ct}$ is the cell count of the control sample at time "t".

Table I presents data on the activity of HHC against various cancer cell lines. MCF-7 cells are human breast adenocarcinoma cells which have some characteristics of differentiated mammary epithelium (i.e., dome formation and estradiol processing via cytoplasmic estrogen receptors). CEM cells are human acute lymphoblastic leukemia cells which morphologically resemble lymphoblastic cells. CEM vinblastin resistant cells contain the P-glycoprotein therefore enabling them to exhibit multidrug resistance to many structurally unrelated compounds. Raji cells are human Burkitt lymphoma cells which are lymphoblast-like. KB cells are human oral epidermoid carcinoma cells. HeLa S3 cells are human cervical pithelioid carcinoma cells.

TABLE I

| Cell type | no. of experiments | $ID_{50}(\mu M)$ | standard deviation |
|---|---|---|---|
| MCF-7[1] | 3 | 1.23 | 0.17 |
| CEM[1] | 4 | 1.97 | 0.34 |
| CEM vin resistant[1] | 4 | 2.61 | 0.33 |
| Raji[2] | 4 | 2.19 | 0.40 |
| KB[1] | 3 | 0.85 | 0.07 |
| HeLa S3[2] | 3 | 1.21 | 0.03 |

[1]period of incubation = 48 h; [2]period of incubation = 24 h.

As the results indicate, HHC is an effective and potent cytostatic agent with respect to a wide variety of cancer cell types.

Example II

Cytotoxic Activity

HHC was tested for cytotoxic activity using a colony formation assay, using an 18 hour pulse exposure. The purpose of the clonogenic assay is to determine the concentration of HHC at which 50% of cell growth is inhibited (i.e., $IC_{50}$) when cells are exposed to the HHC for a defined amount of time (i.e., a pulse exposure to the xenobiotic).

Five ml of a mixture of $2 \times 10^5$ cells/ml (MCF-7 cells) were placed in each of 4 T-25 flasks in a media of RPMI (Gibco). The cells were incubated at 37° C. under 5% $CO_2$ for a minimum of 14 hours to allow the cells to attach. The cells were pulsed for 18 hours with HHC concentrations of 0, 1.5, and 25 $\mu$M, or with DMSO.

The media was removed from the flasks (i.e., media with floating cells) and placed in 15 ml polypropylene centrifuge tubes 1–4 (summarized in Table II). The flasks were washed in 1 ml of PBS and the wash was placed in the appropriate tubes 1–4. Tubes 1–4 were centrifuged at 150 rpm and the media was aspirated. Cells were detached from the flasks by pancreatinization. Approximately 1 ml of the cell suspension from the flasks were added to the appropriate tubes (1–4) and the pellet suspended. The cells in tubes 1–4 were pooled with the cells in the flask. The cells were then resuspended.

One ml of cell suspension from the flask was added to the appropriate 10x tube (tubes 5–8) along with 9 ml of media and suspended well. One ml of the suspension in each 10x tube was then placed in the appropriate 50x tube (tubes 9–12) along with 4 ml of media.

TABLE II

| | control[b] | DMSO | 1.5 $\mu$M HHC | 25$\mu$M HHC |
|---|---|---|---|---|
| floating cells | 1[a] | 2 | 3 | 4 |
| 10x dilution | 5 | 6 | 7 | 8 |
| 50x dilution | 9 | 10 | 11 | 12 |

[a]tube no. [b][HHC] = 0

The cells in the original cell suspension (i.e., in the flask) were counted using trypan blue exclusion assay (described in Example II). Based on this count, the number of cells in the 50x tubes were calculated. The volume necessary to acquire approximately 5400 cells was then determined. This volume was removed from the 50x suspension and placed into 50 ml polypropylene tubes (tubes 13–16). Media was added to attai a volume of 18 ml. The cells were then suspended.

Five ml of suspension from each of tubes 13–16 was transferred to 60×15 mm tissue culture dishes (in triplicate). The cells were incubated until colonies of at least 50 cells were present (approx. 6–8 days). The cells were then stained with Giemsa stain (a solution of 1% Giemsa stain (Sigma) in 100% methanol). The culture dishes were removed from the incubator and the media aspirated off. The dishes were washed 2x with phosphate buffered saline (3–4 ml). Three to four ml of 100% ethanol was added to each dish, an amount sufficient to cover the bottom of the dish, covered and allowed to stand for 30 minutes. The stain was washed out with cold $H_2O$. The water was poured off, without loss of colonies. The plates were inverted and allowed to dry. The cells were counted in those colonies which consisted of at least 50 cells. The $ID_{50}$ was determined as described in Example II. The data is shown in Table III.

TABLE III

| Cell type | no. of experiments | $ID_{50}(\mu M)$ | Std. deviation |
|---|---|---|---|
| MCF-7 | 2 | 1.62 | 0.28 |

As the data shows, HHC is able to effectively kill MCF-7 cancer cells at low dosages.

Preliminary data suggests thatthe in vitro $ID_{50}$ of HHC against C1300 cells (mouse neuroblastoma) is approximately 1.94 $\mu$M after 48 hours of continuous exposure.

Example III

In Vivo Studies

The maximal tolerated dose (MTD) of HHC was determined in BDF1 mice by i.p. injection. Mice were able to tolerate the equivalent of 200 $\mu$molar HHC with no apparent side effects.

Example IV

Determination of Mechanism of Action

Fluorescence activated cell sorting (FACS) was used to determine what percentage of cells could be found in the designated cell cycle phase after 48 hours of continuous HHC exposure. There are four distinct phases in the cell cycle which lead to duplication of the cell and its genetic material. In the G0/G1 phase the cell is at rest or is performing miscellaneous biosynthetic functions. During the S phase, DNA synthesis occurs which leads to replication of the chromosomes. G2 is the pre-mitotic interval while the M phase is the time during which the cell divides.

Cells were exposed to concentrations of 1.5 $\mu$M and 25 $\mu$M of HHC, and DMSO. DMSO had no significant effect on the cell cycle, with a profile almost identical to that of the "no drug" control. The results indicate that low [HHC]'s (i.e., 1.5 $\mu$M) increase the number of cells in G0/G1 and decrease the number of cells in S phase. At high [HHC]'s (i.e., 25 $\mu$M) there is a decrease in the number of cells in G0/G1 and an increase in the number of cells in S phase. This indicates that HHC has an apparent effect upon the G1-S phase transition of the cell cycle.

Example V

Antibacterial Activity (*Staphylococcus aureus*)

A single colony of *Staphylococcus aureus* was grown in 2 ml of Luria-Bertani (LB) broth overnight at 37° C. in a bacterial shaker with vigorous shaking. 0.5 ml of the culture was transferred to 250 ml LB and allowed to grow at 37° C. until the OD600 (optical density) reading was about 0.2 (a reading of 1 OD600 indicates a cell concentration of approximately 8×10$^8$ cells/ml). Cultures were aliquoted into 50 ml tubes containing 13 ml of bacterial culture per tube. 0.5, 1.0, 2.5, 5.0, 10 and 25 $\mu$M of HHC was added to the tubes. No-drug and DMSO solvent were used as controls. Aliquots of the bacterial culture were taken every 2 hours to obtain the OD600 reading. As the results indicate (FIG. 1) HHC is an effective inhibitor of bacterial growth.

Example VI

Antibacterial Activity (*M. tuberculosis*)

Drug susceptibility was tested using the BACTEC method (Siddigi, BACTEC TB System Product and Procedure Manual, Becton Dickinson Corp (1989); Inderlied, *Antimycobacterial Agents in Antibiotics in Laboratory Medicine*, ed. Lorian, 3rd edition, Williams and Wilkins). The growth curve of mycobacteria in liquid media with and without HHC is plotted for 4 to 12 days. Resistance is determined by modification of the 1% proportional method. The control vial is inoculated with a 1:100 dilution of organisms, and a growth rate greater than vials with HHC is interpreted as evidence of susceptibility. Resistance occurs where less than 99% of the organisms are inhibited by the HHC.

Materials:
1) BACTEC 12B vials
2) HHC
3) Special Diluting Fluid (DF): 0.2% fatty acid free bovine serum albumin and 0.02% polysorbate 80 in distilled water, adjusted to pH 6.8±0.2 dispensed and sterilized in the following alloquots: a) 3.0 ml with 8–10 glass beads (1–2 mm/ea); b) 1.5 ml; c) 9.9 ml; and d) 9.0 ml
4) 0.5 McFarland standard in the same tube as (3) above
5) disposable sterile culture loops
6) 1.0 ml tuberculin syringes with fixed 22–26 gauge needle
7) individually packaged alcohol wipes
8) Vortex mixer
9) ATCC 27294 (S.I.R.E. susceptible *M. tuberculosis*)

A quantity of growth of ATCC 27294 is removed from the solid media with a sterile applicator stick and placed in a tube with glass beads and DF. Vortex is used to emulsify bacterial clumps. 0.1 ml of this suspension is used to inoculate new, pre-gassed BACTEC vials. The vials are incubated at 37° C. and monitored daily. The culture is ready for inoculation into the HHC and control vials on the day when the growth index (GI) reaches 900–999.

Vials that have been at 999 for more than one day should not be used, as the bacterial load may be too high. Control vials, inoculated with growth below an index of 900, do not reliably reach the test cutoff value of 30 in the required 12 day experimental period. Serial BACTEC-to-BACTEC transfers of the ATCC organisms are acceptable within the confines of the experimental period.

BACTEC vials are run on the BACTEC instrument to establish proper $CO_2$ levels. The HHC is inoculated aseptically (0.1 ml HHC solution/vial) into labeled vials. Each HHC vial, and one DF vial containing 9.9 ml DF, is inoculated with 0.1 ml of the ATCC BACTEC culture. The DF vial, now containing a 1:100 dilution of the bacterial suspension, is inverted 10× to mix and 0.1 ml withdrawn to inoculate the control 12B vial. A 1:10 control is made in the same manner as above, using a vial with 9.0 ml DF and 1.0 ml of the ATCC BACTEC culture. All test vials are incubated at 37° C.±1° C. for 4 to 12 days, with daily reading on the BACTEC instrument. The vials must be run at approximately the same time each day.

The test is finished when the GI of the control vial reaches 30 and at least days have transpired. The change in GI from one reading to another (delta change) is indicative of the growth rate. If the change is greater in the HHC vial compared to the control, the isolate is resistant to the HHC; if about the same, the isolate is borderline in susceptibility; and if less than the control, the isolate is susceptible to HHC. If the GI in the HHC vials is initially very high (>300) and the GI in the control is low, the inoculum probably included clumps, and the test needs to be repeated. If the GI in a particular HHC vial has reached 500 and then declines when the control reaches 30, the isolate is considered resistant to HHC. If the GI in a HHC vial reaches 900 and then declines before the control reaches 30, the isolate is considered resistant. If the GI of a vial reaches 999 before the control reaches 30, the inoculum was too heavy, and the test needs to be repeated. If the GI reaches 999 on the same day as the control reaches 30, and the delta GI is greater than the control, resistance can be reported. However susceptibility cannot be determined with a reading of 999, and the test would need to be repeated. If the delta GI for the HHC vial is close (10%) to the delta GI of the control this indicates partial resistance, and additional readings (1–3 days) should be taken. The 1:10 control is not used as part of a standard 1% proportional method, but is included here to measure smaller drug effects that may not be apparent with the standard 1% method.

Example VII

Activity of HHC Against Leishmania

Direct susceptibility of leishmania was examined using gross inhibition. After 6 and 24 hours exposure of leishmania to HHC, leishmania were fixed using formaldehyde and cells were counted on a hemacytometer. The results showed that after 24 hours exposure to 2.5 $\mu$M HHC, 90% of leishmania growth was inhibited.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A pharmaceutical composition comprising an amount of a compound of formula (I):

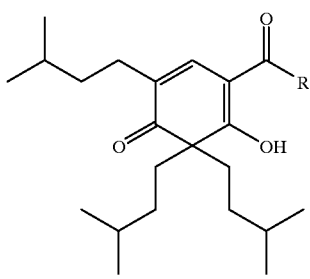

(I)

wherein R is $(C_5-C_8)$alkyl, or a pharmaceutically acceptable salt thereof, effective to inhibit the growth of mycobacterium avium complex, and a pharmaceutically acceptable carrier.

2. The composition of claim 1 wherein the composition is in unit dosage form.

3. The composition of claim 1 comprising two or more compounds of formula (I).

4. A method for inhibiting the growth of mycobacterium avium complex bacteria complrising contacting the bacteria with an effective amount of a compound of formula (I):

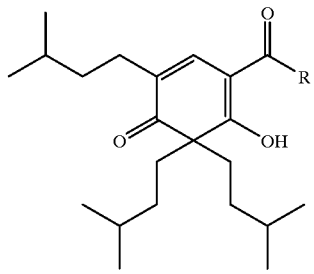

(I)

wherein R is $(C_3-C_8)$alkyl; or a pharmaceutically acceptable salt thereof, effective to inhibit the growth of mycobacterium avium complex bacteria.

5. The method of claim 4 wherein R is —CH(CH$_3$)$_2$.

6. The method of claim 4 wherein R is —CH$_2$CH(CH$_3$)$_2$, or —CH(CH$_3$)CH$_2$CH$_3$.

7. A therapeutic method for inhibiting the growth of mycobacterium avium complex bacteria in a mammal comprising administering to the mammal an effective amount of a compound of formula (I):

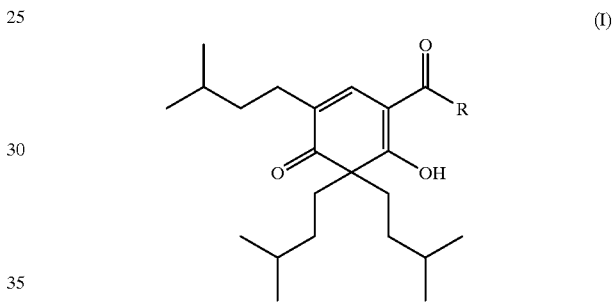

(I)

wherein R is $(C_3-C_8)$alkyl; or a pharmaceutically acceptable salt thereof, effective to inhibit the growth of mycobacterium avium complex bacteria in a mammal.

8. The method of claim 7 wherein R is —CH(CH$_3$)$_2$.

9. The method of claim 7 wherein R is —CH$_2$CH(CH$_3$)$_2$, or —CH(CH$_3$)CH$_2$CH$_3$.

* * * * *